US00PP35836P3

(12) United States Plant Patent
Gordon

(10) Patent No.: US PP35,836 P3
(45) Date of Patent: May 28, 2024

(54) ***CANNABIS* PLANT NAMED 'OT-1'**

(50) Latin Name: *Cannabis sativa*
Varietal Denomination: OT-1

(71) Applicant: Matthew Gordon, Oak Harbor, WA (US)

(72) Inventor: Matthew Gordon, Oak Harbor, WA (US)

(73) Assignee: Matthew Gordon, Oak Harbor, WA (US)

( * ) Notice: Subject to any disclaimer, the term of this patent is extended or adjusted under 35 U.S.C. 154(b) by 0 days.

(21) Appl. No.: 17/803,798

(22) Filed: Nov. 29, 2022

(65) Prior Publication Data

US 2023/0132405 P1 Apr. 27, 2023

Related U.S. Application Data

(63) Continuation-in-part of application No. 17/119,215, filed on Dec. 11, 2020, now abandoned.

(60) Provisional application No. 62/947,516, filed on Dec. 12, 2019.

(51) Int. Cl.
*A01H 5/02* (2018.01)
*A01H 6/28* (2018.01)

(52) U.S. Cl.
USPC ..... Plt./258
CPC ..... *A01H 6/28* (2018.05)

(58) Field of Classification Search
USPC ..... Plt./258, 263.1
CPC ... A01H 5/12; A01H 5/02; A01H 5/00; A01H 5/10; A01H 6/28; A01H 1/101
See application file for complete search history.

(56) References Cited

PUBLICATIONS

HYTIVA Mendocino Purps retrieved on Dec. 13, 2023 at https://www.hytiva.com/strains/hybrid/mendocino-purps, 5 pp. (Year: 2023).*

* cited by examiner

*Primary Examiner* — June Hwu
(74) *Attorney, Agent, or Firm* — Hunt IP Law

(57) ABSTRACT

The unique annual herbaceous *Cannabis* plant variety 'OT-1' is provided. The variety is a selection intended for use as medical oil, and medicinal herb for sale in *Cannabis* dispensaries and as a home garden plant.

6 Drawing Sheets

Latin name of the genus and species:
Genus—*Cannabis.*
Species—*sativa.*
Variety denomination: The new *Cannabis* plant claimed is of the variety denominated 'OT-1'.

BACKGROUND OF THE INVENTION

Field of the Invention

The present invention relates to a new and distinct annual variety of *C. sativa* hybrid, which has been given the variety denomination of 'OT-1'. 'OT-1' is intended for use as medical oil, and medicinal herb for sale in *Cannabis* dispensaries-and as a home garden plant.

Background of the Related Art

The genus *Cannabis* has been in use by humans for millennia, due to the multiplicity of its benefits to humans, including the considerable value and utility of its fiber, the nutritional value of its seeds, and the medicinal value of its floral parts and products made from them. Currently the genus is under intense legal commercialization in the United States as industrial hemp for a variety of purposes including biodegradable plastics and building materials, clothing, paper, food, fuel, and medicines.

Cannabidiol (CBD) extracted from *Cannabis* is widely used in over-the-counter medicines and topical treatments and is also the active ingredient in the FDA-approved drug Epidiolex®. CBD is just one of at least dozens—perhaps hundreds—of cannabinoids endogenous to *Cannabis*, tetrahydrocannabinol (THC) being the other cannabinoid that is most well-known. The cannabinoids as a group interact with the human endocannabinoid receptors, which are distributed in the brain and throughout the body. The study of the endocannabinoid system (ECS) in humans and other mammals is an area of increasing interest and holds tremendous promise for the future of medicine. See, e.g., Russo (2019). *Cannabis* and Pain, *Pain Medicine,* 20(10): 1;20(11):2083-2085; and Russo (2016). Clinical Endocannabinoid Deficiency Reconsidered: Current Research Supports the Theory in Migraine, Fibromyalgia, Irritable Bowel, and Other Treatment-Resistant Syndromes, *Cannabis Cannabinoid Res.* 1(1): 154-165.

Non-hemp forms of *Cannabis*, frequently referred to as marijuana, have been legalized for medicinal use in many states and for recreational use (sometimes called "adult use") in a growing number of states. It is expected that the wave of legalization will continue to the point of some form of federal legalization or decriminalization.

Typically, marijuana products are available to users for purchase in specialized "dispensaries" that offer dried flower, edibles, tinctures, extracts, and the like. In some cases, a unique or unusual chemical profile, or chemotype, is attractive not only for flower sales but also for use in the preparation of extracts and/or isolates and for the manufacture of a variety of products that possess characteristics of the chemotype.

SUMMARY OF THE INVENTION

The present invention relates to a new and distinct annual variety of *C. sativa*, which has been given the variety denomination of 'OT-1'. 'OT-1' is intended for use as medical oil, and medicinal herb for sale in *Cannabis* dispensaries and as a home garden plant. Plants of the new cultivar were developed to remove negative effects such as fatigue, increased appetite, anxiety, memory loss, etc., that are experienced by a consumer of the plant.

'OT-1' originated in Burlington Washington, in 2005. The parents are of an unknown strain derived from "bagseed" found in flower purchased for consumption. It is believed to be related to 'Mendo Purps' (unpatented). Buds of 'OT-1' are less dense than many *Cannabis* cultivars, similar to 'Mendo Purps'. 'OT-1' is less purple than 'Mendo Purps', but is otherwise similar in appearance, with most of the differences between 'Mendo Purps' and 'OT-1' being chemotypic.

The variety was originally grown from a seed and then cloned. The clones were self-crossed for 13 generations, and offspring of those crosses were selected for efficacy in ameliorating memory loss. Several sibling crosses within a generation were conducted using the same selection criteria, seeking to combine the favorable effects of each. Each generation produced approximately 50-150 plants which were screened. At certain stages, when a combination of desired traits was achieved in a given plant, such plant was backcrossed to a parental or grandparental generation to obtain higher expression.

The variety was propagated asexually at Oak Harbor, Island County, WA between 2012 and 2018 and showed a uniformity in the population. Asexual reproduction of the new variety has demonstrated that the new variety reproduces true to type with all of the morphological characteristics, as herein described, firmly fixed and retained through successive generations of such asexual propagation. Chemotypic characteristics of each new variety are variable based upon cultivation conditions, as is typical of *Cannabis* plants. Accordingly, while chemotypic information provided herein is representative of performance of the new varieties under a particular set of cultivation conditions, it is not limiting on other chemotypic profiles obtainable under a different set of cultivation conditions. Table 1 and Table 2 provides exemplary profiles as determine by a testing laboratory using methods such as high-performance liquid chromatography (HPLC) and gas chromatography with mass spectrometry Due to the natural variability of chemotypic expression that is commonly observed in *Cannabis* plants, arising from numerous causes such as cultivation conditions, the values set forth in the tables do not reflect the only possible range of outcomes that can be obtained from plants of the new variety. Thus, these values are merely exemplary of observed values (middle column) and predicted normal variations from the observed values.

TABLE 1

Exemplary Profiles of Key Cannabinoids.

| | Percent | Percent | Percent |
|---|---|---|---|
| THCA | 11.456 | 14.32 | 17.184 |
| Total THC | 10.312 | 12.89 | 15.468 |
| Total CBD | 0.04 | 0.05 | 0.06 |
| d9-THC | 0.264 | 0.33 | 0.396 |
| CBGA | 0.728 | 0.91 | 1.092 |
| Total Cannabinoid | 12.528 | 15.66 | 18.792 |

*Total THC = (THCA * 0.877) + THC (i.e. delta 9 THC) + delta 8 THC

TABLE 2

Exemplary Profiles of Key Terpenes.

| | Percent | Percent | Percent |
|---|---|---|---|
| Alpha Pinene | 0.0408 | 0.051 | 0.0612 |
| Fenchol | 0.0544 | 0.068 | 0.0816 |
| Terpineol | 0.044 | 0.055 | 0.066 |
| Alpha Humulene | 0.2016 | 0.252 | 0.3024 |
| (-)-Caryophyllene | 0.0184 | 0.023 | 0.0276 |
| Ocimene | 0.0336 | 0.042 | 0.0504 |
| Eucalyptol | 0.16 | 0.20 | 0.24 |
| Phytol | 0.0688 | 0.086 | 0.1032 |
| beta Myrcene | 0.0248 | 0.031 | 0.0372 |
| Limonene | 0.38 | 0.475 | 0.57 |
| Linalool | 0.0184 | 0.023 | 0.0276 |
| beta Caryophyllene | 0.392 | 0.490 | 0.588 |
| (-)-alpha Bisabolol | 0.0536 | 0.067 | 0.0804 |
| beta Pinene | 0.06 | 0.075 | 0.09 |

BRIEF DESCRIPTION OF THE DRAWINGS

The accompanying photographic illustrations show the typical appearance of the new variety 'OT-1'. The colors are as nearly true as is reasonably possible in a color representation of this type. Colors in the photographs may differ slightly from the color values cited in the detailed botanical description which accurately describes the colors of the new plant.

DETAILED BOTANICAL DESCRIPTION

Figure 1:
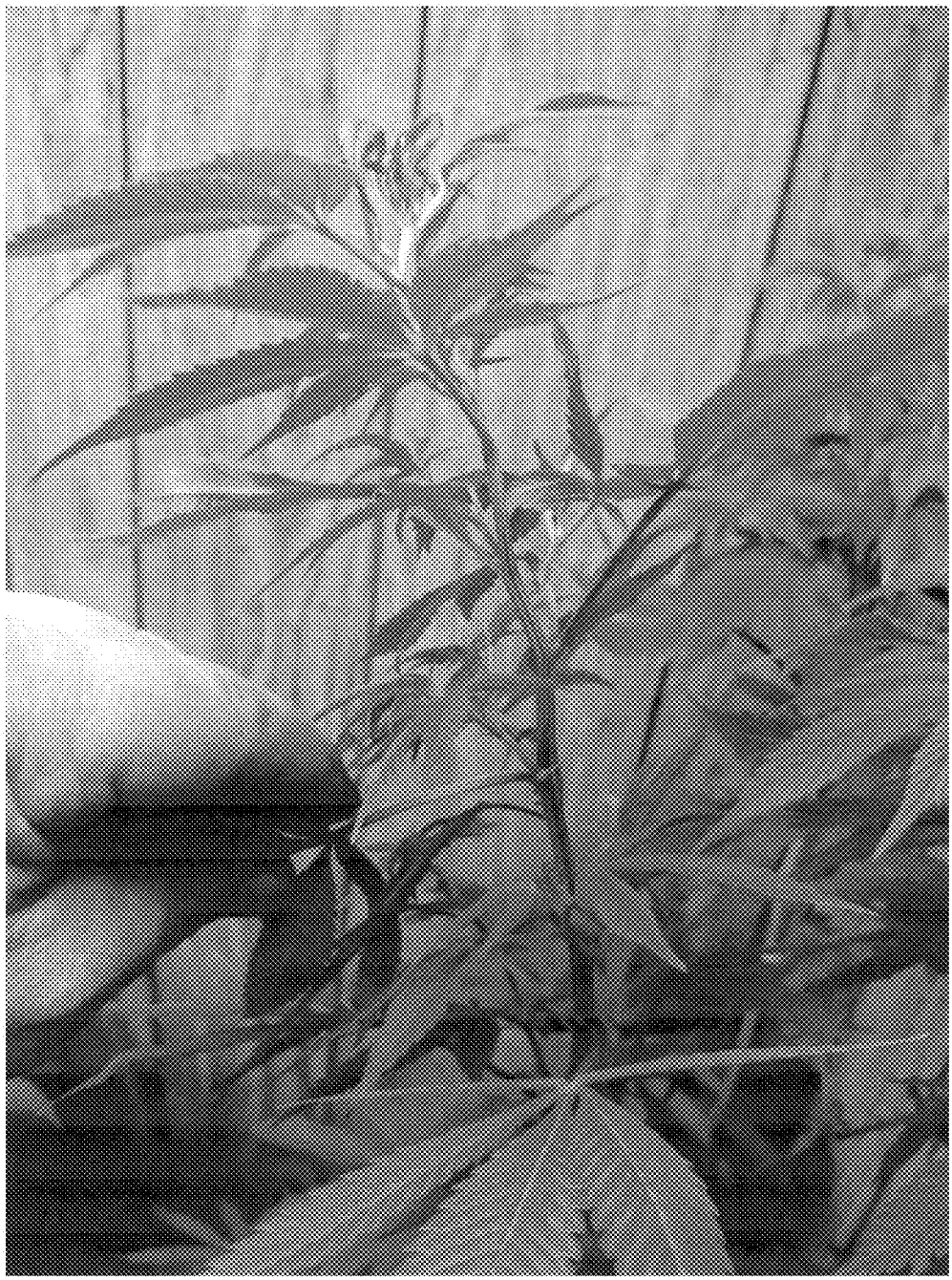
FIG. 1 is photograph of the plant at 6 weeks of age.
Figure 2:
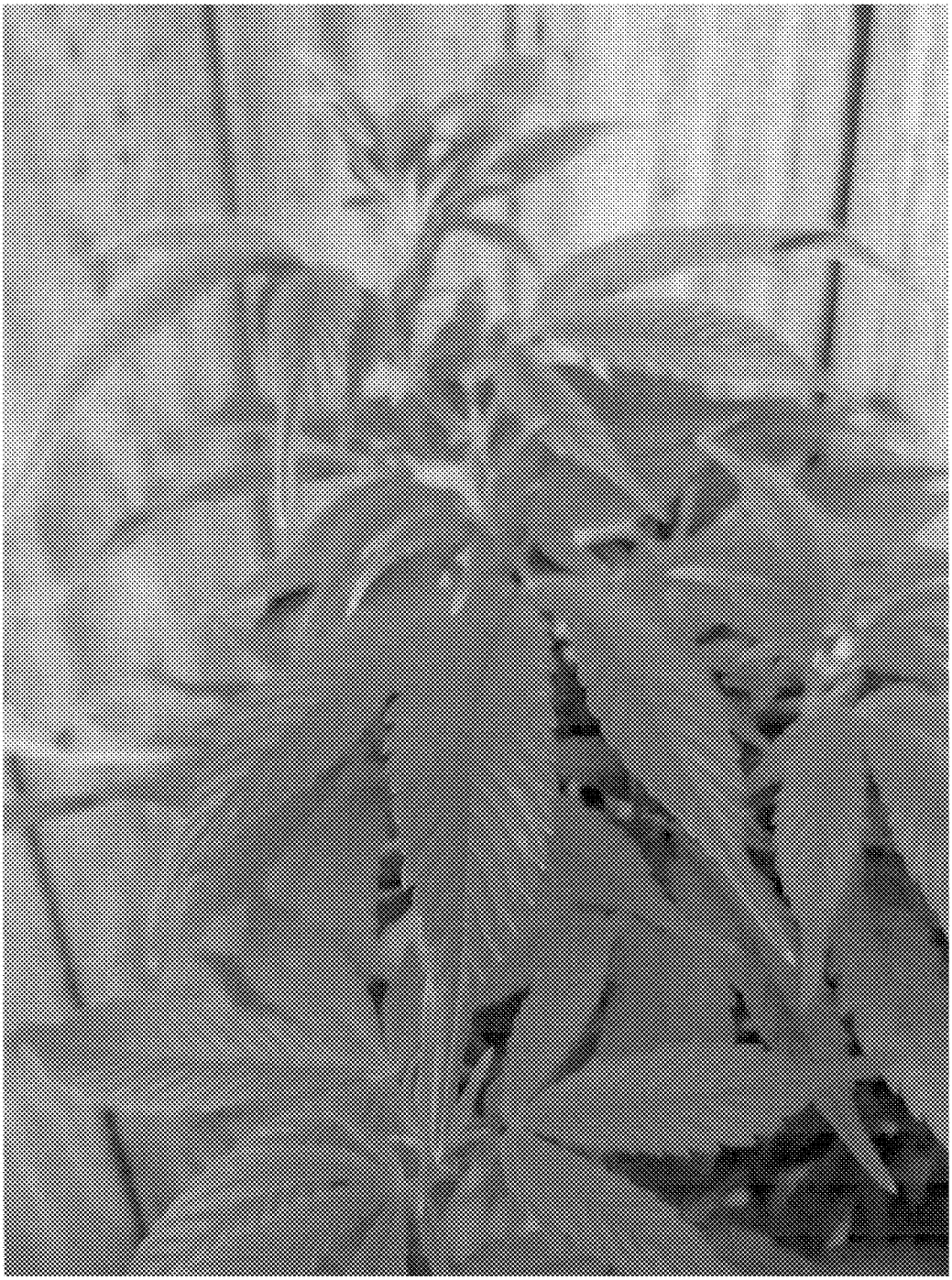
FIG. 2 is photograph of the plant at 6 weeks of age.
Figure 3:
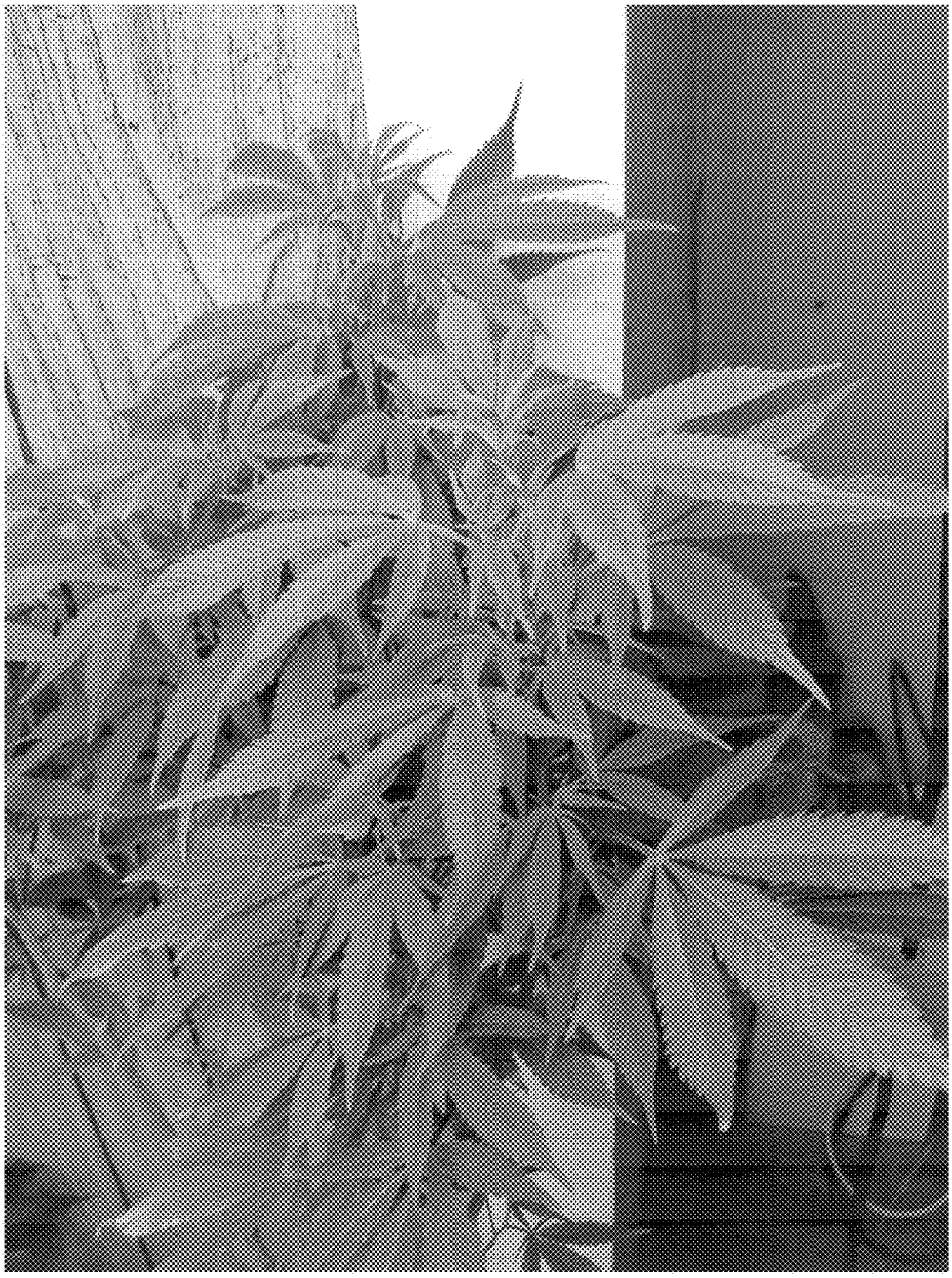
FIG. 3 is photograph of the plant at 6 weeks of age.
Figure 4:
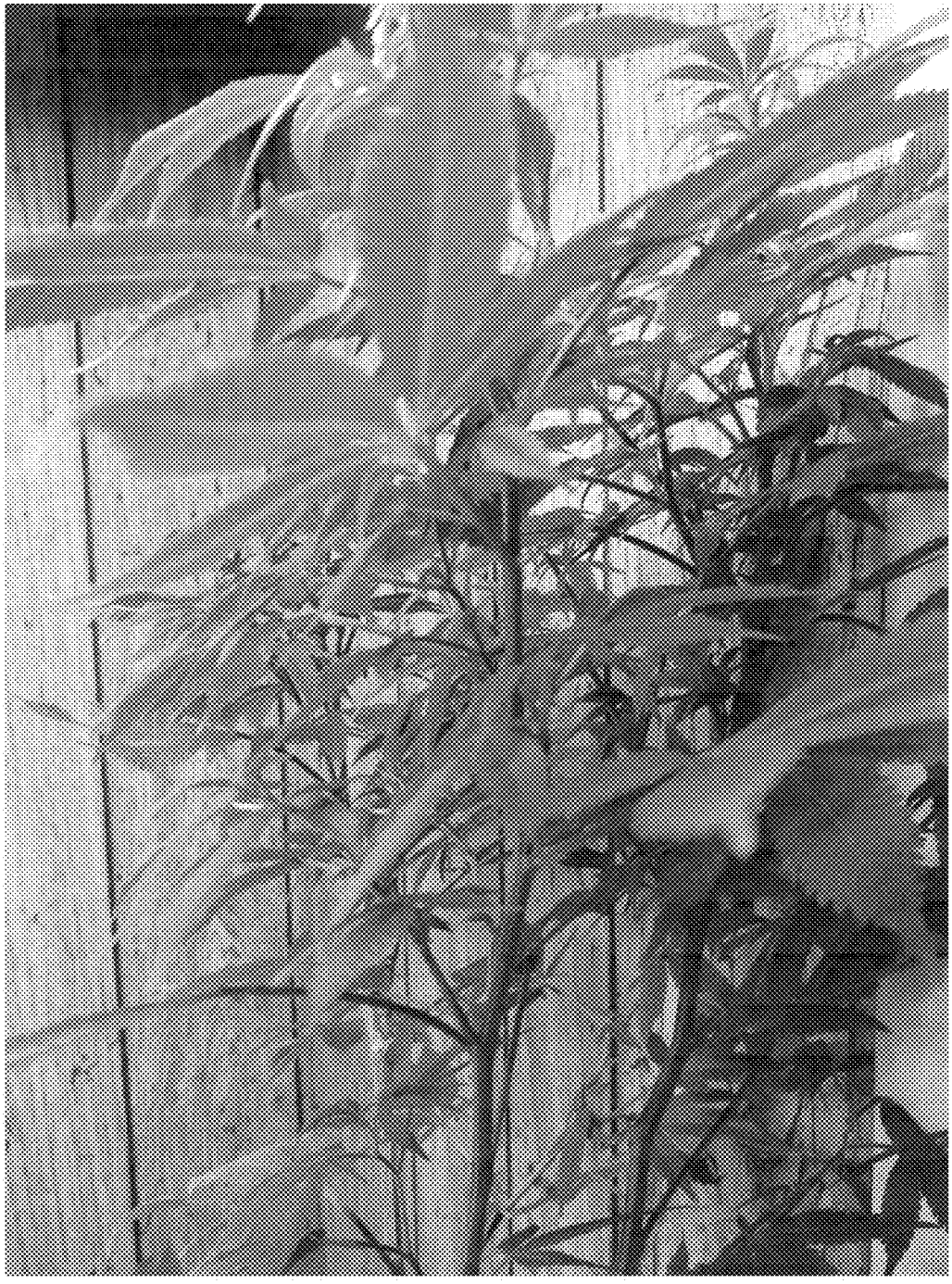
FIG. 4 is photograph of the plant at 6 weeks of age.
Figure 5:
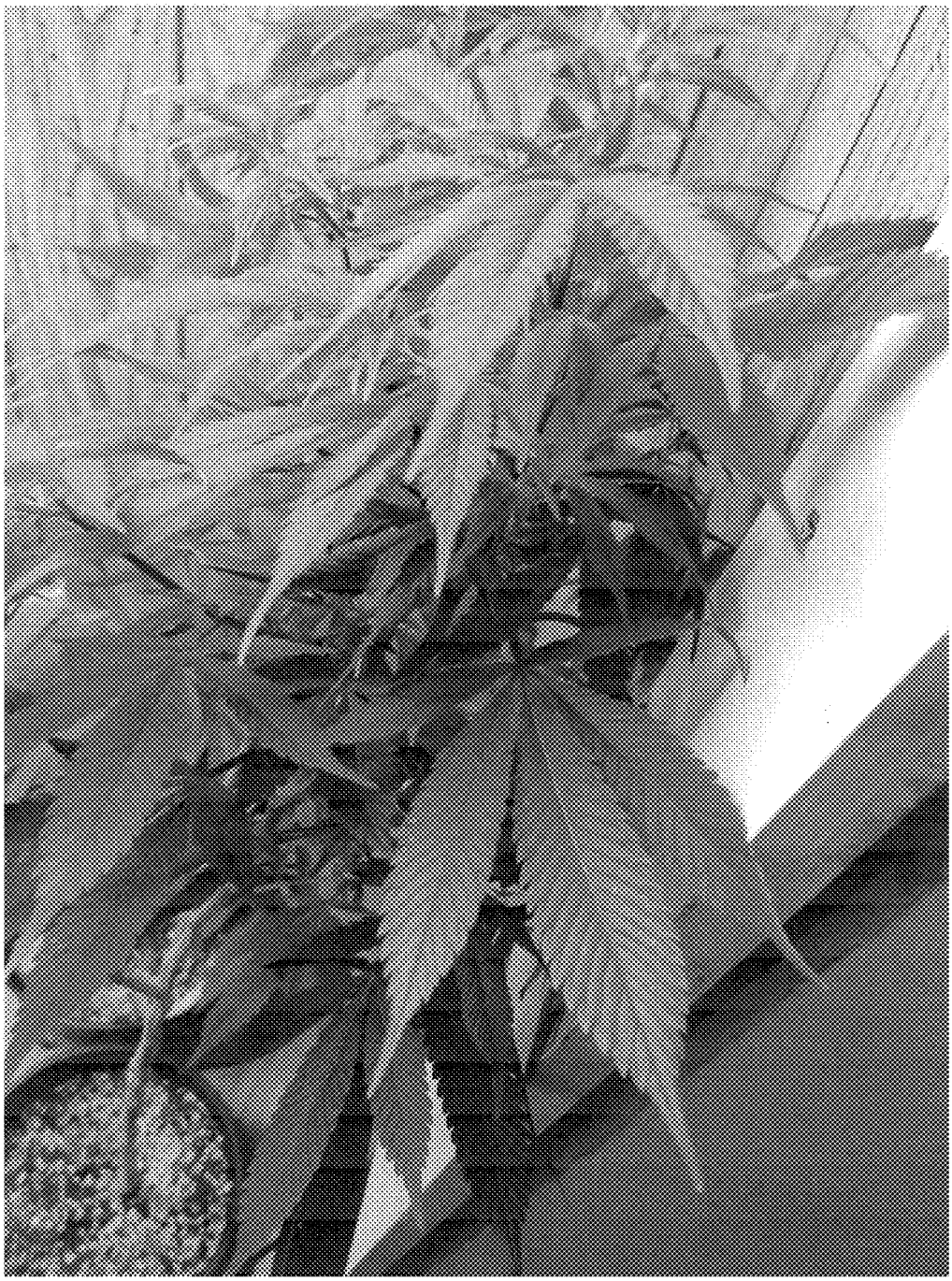
FIG. 5 is photograph of the plant at 6 weeks of age.
Figure 6:
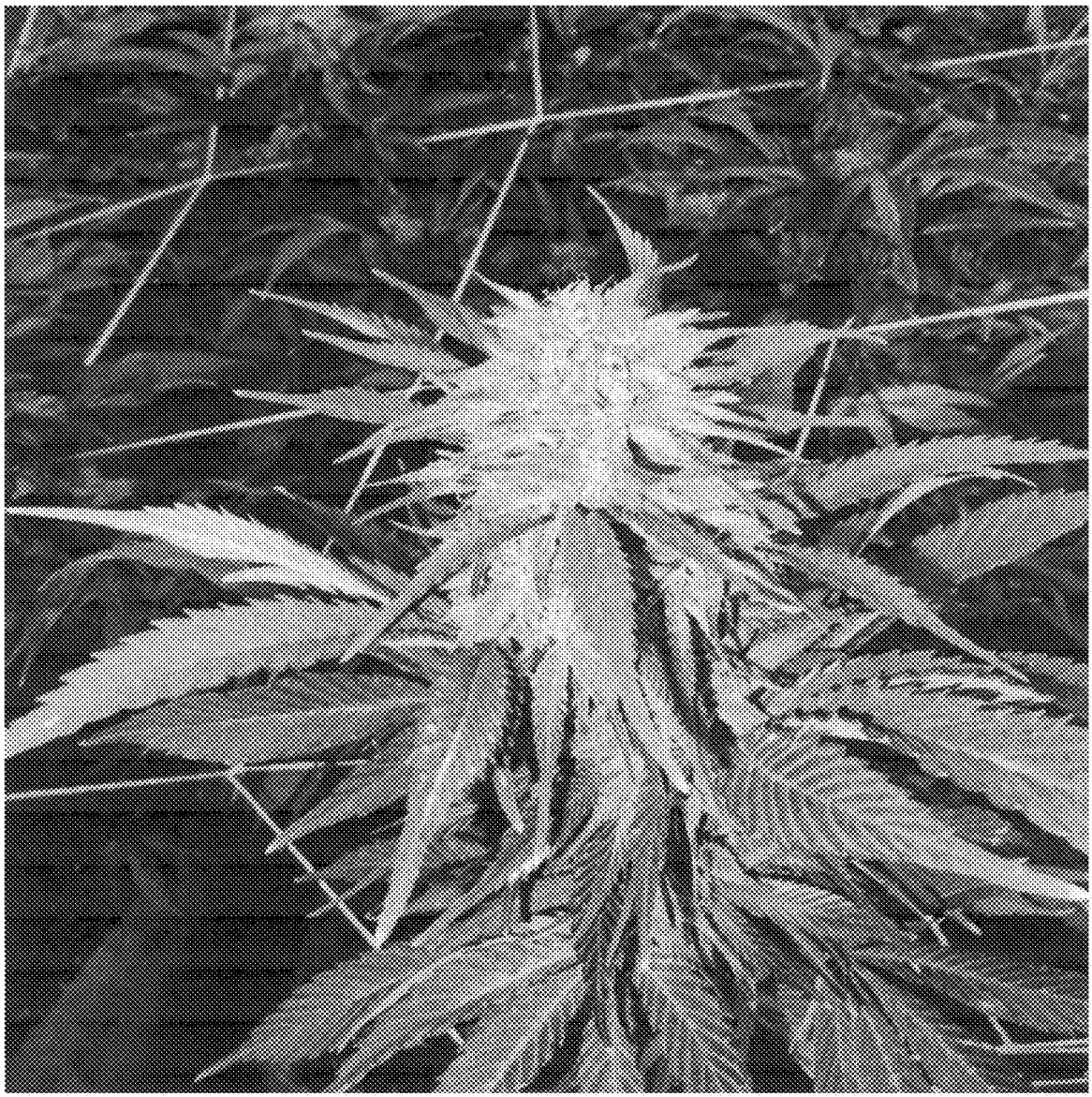
FIG. 6 is a photograph of the inflorescence of the plant.

The following detailed description sets forth the distinctive characteristics of 'OT-1'. The data which defines these characteristics was collected from asexual reproductions of the original selection. Dimensions, sizes, colors, and other characteristics are approximations and averages set forth as accurately as possible. The plant history was taken on mother plants approximately six months old, and the descriptions relate to plants grown outdoors in Whidbey Island, Washington or in Salem, Oregon. Color notations are in reference to hexadecimal color values known to those of ordinary skill in internet website design.

Type: Herbaceous annual.

Classification:

a. *Family.*—Cannabaceae.
b. *Genus.*—*Cannabis.*
c. *Species.*—*Sativa.*
d. *Common name.*—Marijuana.

Parentage: Unknown.

Market class: Medical oil and medicinal herb.

PLANT

General:

a. *Hardiness.*—High resistance to heat stress: thriving in over 110° heat and high resilience to cold: 2 weeks with night-time temperatures below 28° F. during flowering outdoors in Oregon in November.
b. *Average height.*—6-8 ft in a 30-gallon pot.
c. *Average spread.*—6-8 ft in a 30-gallon pot.

d. *Growth rate*.—Highly variable: depends on feeding intensity; grows slowly when lightly fed, more rapidly when heavily fed (light feeding typically results in better flower quality).
e. *Productivity*.—Heavy yield when plants are grown large (e.g., in 200-gallon pots); approximately 1 pound per foot of height when plants are grown above 10 feet tall with large breadth; plants grown in pots to around six feet in height produce about 1 pound (dry weight) per plant.
f. *Disease resistance/susceptibility*.—Resistant to mildew and *Botrytis cinerea*.
g. *Pest resistance/susceptibility*.—Resistant to spider mites (*Tetranychus urticae*).
h. *Drought tolerance*.—High.
i. *Fragrance*.—Very faint. Hints of grape, pineapple, strawberry, mango, gas, diesel.
j. *Proportion of female plants*.—100%.
k. *Type of inflorescence*.—Cymose.
l. *Photoperiodicity*.—Conversion from vegetative state to flowering with 12/12 light/dark regimen.
m. *Shipping quality*.—Very good.
n. *Market use*.—Production of various forms for consumption.
o. *Storage life*.—Very good. Longer than most other *Cannabis* varieties in a cool dry place vacuum sealed in the dark; after 1.5 years of storage was still fresh and effective with little to no degradation.

STEM/CENTRAL STALK

General:
a. *Average diameter of stem*.—3 in at base and ½ inch near top of a 4 ft stem.
b. *Average length of stem*.—4-8 ft.
c. *Shape*.—Generally cylindrical with vertical grooves.
d. *Average length of internode*.—Depends on position in the plant; internodes are longer near the top of the plant; near the bottom of the plant, internodes are about 3 mm; closer to the top of the plant, internodes are about 18-22 mm.
e. *Depth of grooves*.—Shallow.
f. *Pith in cross section*.—Depends on the life stage of the plant — mature plant is medium pithy, younger stems are substantially woody.
g. *Trichome type*.—Capitate stalked.
h. *Color*.—Ranges from Green (#849249: 132, 146, 73) to Violet (#53455B: 83,69,91).

LEAF

General:
a. *Leaf color* (*top side*).—#4D6221 — Hue: green.
b. *Leaf color* (*under side*).—#667D3A — Hue: green.
c. *Leaf arrangement*.—Opposite.
d. *Leaf shape*.—Tendency to curl — otherwise typical of a *Cannabis* plant, first three middle leaflets in each leaf are generally similar in length, others outside are shorter.
e. *Leaf apex shape*.—Accuminate.
f. *Leaf base shape*.—Acute.
g. *Average leaf width*.—13 cm.
h. *Average leaf length*.—12-21 cm.
i. *Number of leaflets per leaf* —5-7.
j. *Central leaflet length*.—13 cm.
k. *Central leaflet width*.—3 cm.
l. *Number of teeth/serrations in the middle of leaflet*.—11.
m. *Margin type*.—Serrate.
n. *Trichome type* (*top surface*).—Capitate stalked.
o. *Trichome type* (*bottom surface*).—Capitate stalked.
p. *Texture of top and bottom surfaces*.—Rough.
q. *Fragrance*.—Leaves have little to no fragrance.

PETIOLE

General:
a. *Length* —7 cm.
b. *Diameter*.—8 mm.
c. *Surface texture*.—Rough, grooved.
d. *Strength*.—Strong.
e. *Anthocyanin intensity*.—Medium.
f. *Trichome type*.—Capitate stalked.

PEDICEL

General:
g. *Length*.—8 mm.
h. *Diameter*.—3 mm.
i. *Surface texture*.—Rough.
j. *Strength*.—Strong.
k. *Anthocyanin intensity*.—Weak.
l. *Color*.—Green (#799343: 121, 147, 67)

FEMALE FLOWER

General:
a. *Time of flowering*.—70-75 days.
b. *Fragrance*.—Very faint fragrance: lime, pine, eucalyptus/herbal odor; very faint very unique medicinal/antiseptic odor.
c. *Bract*.—
  i. *Shape*.—Urceolate.
  ii. *Trichome type*.—Capitate stalked.
  iii. *Color*.—Ranges from Green (#769241: 118, 146, 65) to Blue (#848899: 132, 136, 153).
  iv. *Average Length*.—5 mm-6 cm.
  v. *Average Quantity*.—15-30 per inflorescence.
d. *Bracteole*.—
  i. *Length*.—about 9 mm-1 cm.
  ii. *Shape*.—Beaked.
  iii. *Trichome type*.—Capitate stalked.
  iv. *Color*.—Violet (#5F4872: 95, 72, 114).
e. *Stipule*.—
  i. *Length*.—0.4-1.5 cm.
  ii. *Shape*.—Acute tip.
  iii. *Color*.—Green (#5C7B34: 92, 123, 52).

SEEDS

General:
a. *Shape*.—Ovoid.
b. *Length*.—3 mm.
c. *Width*.—2 mm.
d. *Weight per* 1000 *seeds*.—*About* 18.1 g.
e. *Color of testa*.—Variable yellow, green, brown (specific color reading unattainable due to variability and small size of testa).
f. *Marbling*.—Weak.

PEDUNCLE

General:
a. *Length*.—3 cm.
b. *Trichome type*.—Capitate stalked.
c. *Color*.—Ranges from Green (#849249: 132, 146, 73) to Violet (#53455B: 83,69,91).

The invention claimed is:

1. A new and distinct variety of *Cannabis* plant named 'OT-1', as illustrated and described herein.

* * * * *